United States Patent [19]
Kugo et al.

[11] Patent Number: 5,522,832
[45] Date of Patent: Jun. 4, 1996

[54] BLOOD VESSEL PIERCING INSTRUMENT

[75] Inventors: Takahiro Kugo; Yukihiko Murata; Chitoshi Kamiya, all of Fujinomiya; Kihoshi Yamauchi; Hiroshi Ishikawa, both of Sendai, all of Japan

[73] Assignees: Terumo Kabushiki Kaisha, Tokyo; Tokin Corporation, Sendai, both of Japan

[21] Appl. No.: 186,594

[22] Filed: Jan. 26, 1994

[30] Foreign Application Priority Data

Jan. 26, 1993 [JP] Japan ................................... 5-031474

[51] Int. Cl.⁶ .................................................. A61B 17/34
[52] U.S. Cl. ............................................ 606/185; 604/282
[58] Field of Search ............................... 606/167, 181, 606/184, 185; 604/51, 52, 158, 164, 165, 171, 264, 272, 273, 282

[56] References Cited

U.S. PATENT DOCUMENTS

| | | | |
|---|---|---|---|
| 3,565,074 | 2/1971 | Foti . | |
| 4,317,445 | 3/1982 | Robinson | 604/264 |
| 4,840,622 | 6/1989 | Hardy | 604/264 |
| 5,011,478 | 4/1991 | Cope | 604/264 |
| 5,180,376 | 1/1993 | Fischell | 604/282 |
| 5,263,937 | 11/1993 | Shipp | 604/272 |
| 5,350,393 | 9/1994 | Yoon | 606/185 |

FOREIGN PATENT DOCUMENTS

0437795A1  7/1991  European Pat. Off. .

Primary Examiner—Stephen C. Pellegrino
Assistant Examiner—Glenn Dawson
Attorney, Agent, or Firm—Burns, Doane, Swecker & Mathis

[57] ABSTRACT

A blood vessel piercing instrument includes an outer tube assembly and an inner needle assembly. The outer tube assembly has an outer tube and an outer tube hub attached to the rear end portion of said outer tube. The outer tube has a metal tubular member made of a superelastic metal and a resin tubular member which covers the outside surface of the metal tubular member and has the front end portion extending beyond the front end of the metal tubular member. The inner needle assembly includes an inner needle which is extractably inserted in said outer tube assembly and has a piercing edged surface formed at the front end protruding from said outer tube and an inner needle hub which is attached to the rear end portion of said inner needle and engages with the rear end of said outer tube hub. An inside diameter of said front end portion of said resin tubular member is smaller than the inside diameter of said metal tubular member and substantially equal to an outside diameter of said inner needle.

6 Claims, 11 Drawing Sheets

BLOOD VESSEL PIERCING INSTRUMENT

BACKGROUND OF THE INVENTION

This invention relates to a blood vessel piercing instrument used to introduce into the blood vessel a guide wire for guiding a catheter to a target region in the blood vessel.

Various guide wires and blood vessel piercing instruments for introducing a guide wire into the blood vessel are used. Conventional blood vessel piercing instruments generally comprise an outer tube assembly consisting of an outer tube for introducing a guide wire into the blood vessel and an outer tube hub attached to the rear end portion of the outer tube and an inner needle assembly consisting of an inner needle which is extractably inserted in the outer tube assembly and has a piercing edged surface formed at the front end and an inner needle hub which is attached to the rear end portion of the inner needle and engages with the rear end of the outer tube hub.

In a typical conventional blood vessel piercing instrument 50, the metal inner needle 51 protrudes from the front end of the metal outer tube 52 as shown in FIG. 11, and the outer tube 52 is thrust into the blood vessel along with the inner needle.

In such a conventional blood vessel piercing instrument 50, a step h is formed between the outside surface of the metal inner needle 51 and the front end of the metal outer tube 52. This step often causes a pain to the patients when the instrument is thrust into the blood vessel. However, it is difficult to employ a structure in which the inside surface of the front end of the outer tube comes in close contact with the outside surface of the inner needle in order to eliminate the step because the outer tube is made of a metal. If this structure is used for the metal outer tube which does not expand and has a high frictional resistance, removal of the inner needle will be difficult.

Further, the hard front end of the metal outer tube can cause a damage to the wall of the blood vessel while the outer tube is left inserted in the blood vessel until the outer tube is removed after a guide wire is inserted into the blood vessel. Sometimes, the insertion of a guide wire is difficult or causes a pain to the patient because of an insufficient elasticity of the metal outer tube.

Some conventional blood vessel piercing instruments have the outer tube made of a synthetic resin. The resin outer tube of those conventional blood vessels, however, has not a sufficient strength and can bend in angles or collapse after the inner needle is removed.

SUMMARY OF THE INVENTION

The object of this invention is therefore to provide a blood vessel piercing instrument which has a sufficient strength and does not bend in angles after the inner needle is removed, is easily thrust into the blood vessel with a reduced thrust resistance and without causing a pain to the patient, and has a sufficient elasticity to make easier the insertion of a guide wire and reduce a pain to the patient during the insertion.

This object is achieved by the blood vessel piercing instrument of this invention which comprises an outer tube assembly and an inner needle assembly, said outer tube assembly comprising an outer tube and an outer tube hub attached to the rear end portion of said outer tube, and said outer tube comprising a metal tubular member made of a superelastic or pseudoelastic metal and a resin tubular member which covers the outside surface of the metal tubular member and has the front end portion extending beyond the front end of the metal tubular member, said inner needle assembly comprising an inner needle which is extractably inserted in said outer tube assembly and has a piercing edged surface formed at the front end protruding from said outer tube and an inner needle hub which is attached to the rear end portion of said inner needle and engages with the rear end of said outer tube hub, an inside diameter of said front end portion of said resin tubular member is smaller than the inside diameter of said metal tubular member and substantially or approximately equal to an outside diameter of said inner needle.

DETAILED DESCRIPTION OF THE PREFERRED EMBODIMENTS

Figure 1:
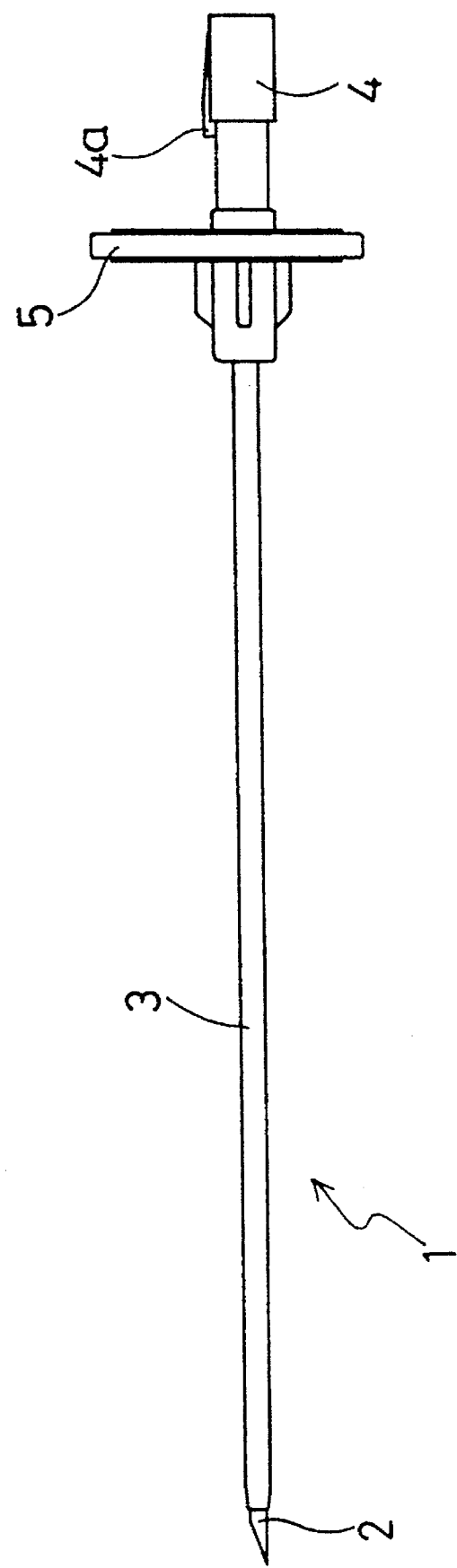
FIG. 1 is an external appearance of the blood vessel piercing instrument of this invention.

The blood vessel piercing instrument of this invention is described below using the embodiment shown in FIGS. 1 and 2.

The blood vessel piercing instrument 1 comprises an outer tube assembly and an inner needle assembly.

The outer tube assembly comprises an outer tube 3 and an outer tube hub 5 attached to the rear end portion of the outer tube 3.

The inner needle assembly comprises a hollow inner needle 2 which is extractably inserted in the outer tube assembly and has a piercing edged surface 2a formed at the front end protruding from the outer tube 3 and an inner needle hub 4 which is attached to the rear end portion of the inner needle 2 and engages with the rear end of the outer tube hub 5.

The outer tube 3 comprises a tubular member 6 made of a superelastic or pseudoelastic metal and a resin tubular member 7 which covers the outside surface of the metal tubular member 6 and has the front end portion extending beyond the front end of the metal tubular member 6. The inside diameter of the front end portion of the resin tubular member 7 is smaller than that of the metal tubular member 6 and substantially or approximately equal to the outside diameter of the inner needle 2.

The inner needle assembly comprises an inner needle 2 and an inner needle hub 4 attached to the inner needle 2 as shown in FIG. 1.

Figure 6:
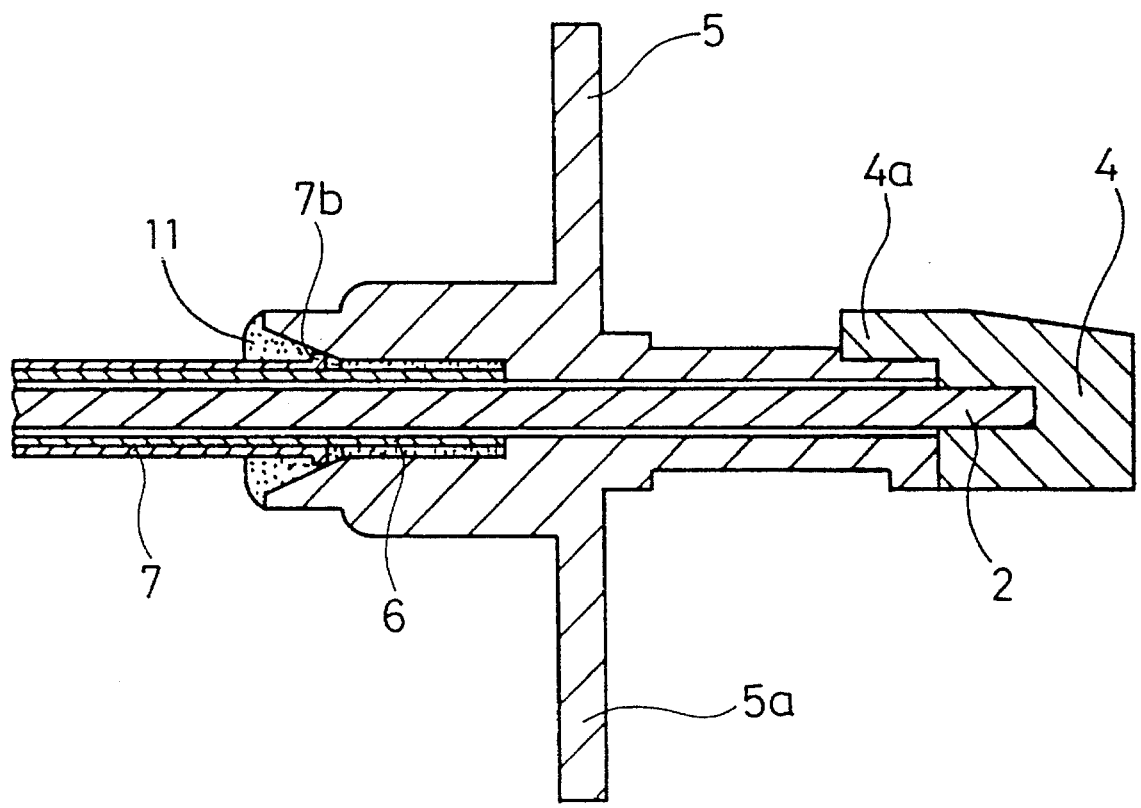
FIG. 6 is a part-sectional enlarged view of the rear end portion of the blood vessel piercing instrument of an embodiment of this invention.

The inner needle 2 has a piercing edged surface 2a formed at the front end and has such a length that it extends through the outer tube 3 and the edged surface 2a protrudes from the front end of the outer tube 3. In this embodiment, a solid needle is used for the inner needle 2. For the material for forming the inner needle 2, stainless steel is preferable. The front end portion of the inner needle hub 4 has preferably a form which can engage with the rear end portion of the outer tube hub 5. The inner needle hub 4 and the outer tube hub 5 are preferably provided with a securing mechanism for stopping the turning movement of the inner assembly and fixing the position of the tip of the piercing edged surface 2a. In this embodiment, the inner needle hub 4 has a projection 4a extending frontward from its front end as shown in FIG. 6 and the outer tube hub 5 has a groove on its rear end portion which receives the projection 4a. These projection 4a and the groove form the securing mechanism.

For the material of the inner needle hub 4, thermoplastic resins (polypropylene, polyethylene, polycarbonate, polystyrene, etc.) and metals (stainless steel, for example) can be used. The joining of the inner needle 2 and inner needle hub 4 may be made by means of an adhesive or solvent. When a thermoplastic material is used for the inner needle hub 4, the inner needle 2 and inner needle hub 4 may also be attached by induction heating the inner needle 2 and fusing the hub 4 by the heat of the inner needle 2.

The outer tube assembly comprises an outer tube 3 and an outer hub 5 attached to the rear end portion of the outer tube 3.

The outer tube 3 is open at the front end to allow the front end of the inner needle 2 to protrude, as shown in FIG. 1. The outer tube 3 consists of a metal tubular member 6 made of a superelastic metal and a resin tubular member 7 which covers the outside surface of the metal tubular member 6 as show in FIG. 2. The front end portion of the resin tubular member 7 extends beyond the front end of the metal tubular member 6. The outside diameter of the front end portion 7a (the portion extending beyond the front end of the metal tubular member 6) becomes gradually smaller toward the front end, and that of the front end becomes steeply smaller. The inside diameter of this front end portion 7a is approximately equal to or a little larger or smaller than the outside diameter of the inner needle 2 so that a step or gap is not formed between the outside surface of the inner needle 2 and the tip of the resin tubular member 7.

Since a step or gap is thus practically not formed between the outside surface of the inner needle 2 and the front end of the outer tube 3, this blood vessel piercing instrument 1 causes less pain to the patient when it is thrust into the blood vessel. Further, since the front end portion of the outer tube 3 is formed of a soft resin, the possibility that the front end of the outer tube 3 may hurt the wall of the blood vessel when the inner needle 2 is pulled off and a guide wire is inserted significantly diminishes. Furthermore, since the front end portion made of a soft resin elastically deforms to accommodate its shape to the wire inserted, insertion of a guide wire is made easier than when the front end portion of the outer tube 3 is made of a metal.

It is preferable to form an annular depression 8 or an annular groove between the front end of the metal tubular member 6 and the inside surface of the front end portion 7a of the resin tubular member 7. By forming such an annular depression 8, the elastic bending of the resin tubular member 7 is made easier. In the blood vessel piercing instrument of the embodiment shown in FIG. 2, the inside surface of the front end of the metal tubular member 6 is so formed that the inside diameter becomes larger toward the front end, by cutting away the inside edge of the front end. The inside surface of the resin tubular member 7 opposite the front end of the metal tubular member 6, on the other hand, is so formed that the inside diameter becomes steeply smaller from around the front end of the metal tubular member 6 toward the front end.

Figure 2:
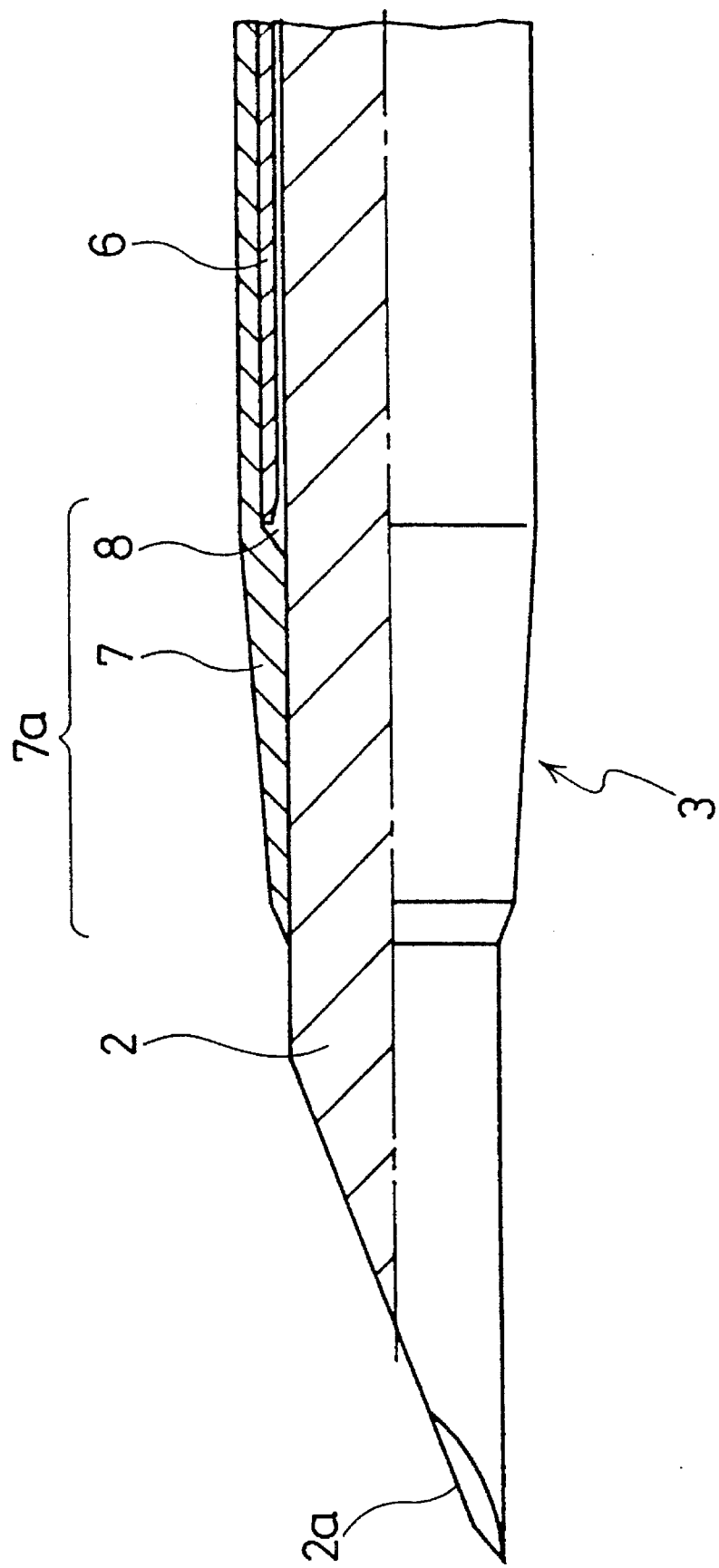
FIG. 2 is a part-sectional enlarged view of the front end portion of the blood vessel piercing instrument of an embodiment of the piercing instrument of this invention.

The outer tube 3 having such an annular depression 8 is made by first placing a half-formed resin tubular member over the metal tubular member 6 with its front end portion extended from the front end of the metal tubular member 6 and then hot forming the half-made resin tubular member into the inside shape as shown in FIG. 2 by means of a metal mold. It can also be made by first forming the resin tubular member 7 with the inside shape as shown in FIG. 2 and then inserting the metal tubular member 6 into the resin tubular member 7.

There may be a little gap between the resin tubular member 7 and the metal tubular member 6 when their rear ends are held respectively by the outer tube hub 5 as shown in FIG. 6. The outer tube 3 can be attached to the outer tube hub 5 by means of an adhesive or by induction heating as mentioned above.

Although, in the blood vessel piercing instrument of this embodiment, the entire inside surface of the front end portion 7a of the resin tubular member 7 has a substantially uniform diameter and is in contact with the outside surface of the inner needle 2, the front end portion 7a may also be in such a form that only the inside surface of its short front end portion is in contact with the outside surface of the inner needle 2.

Figure 3:
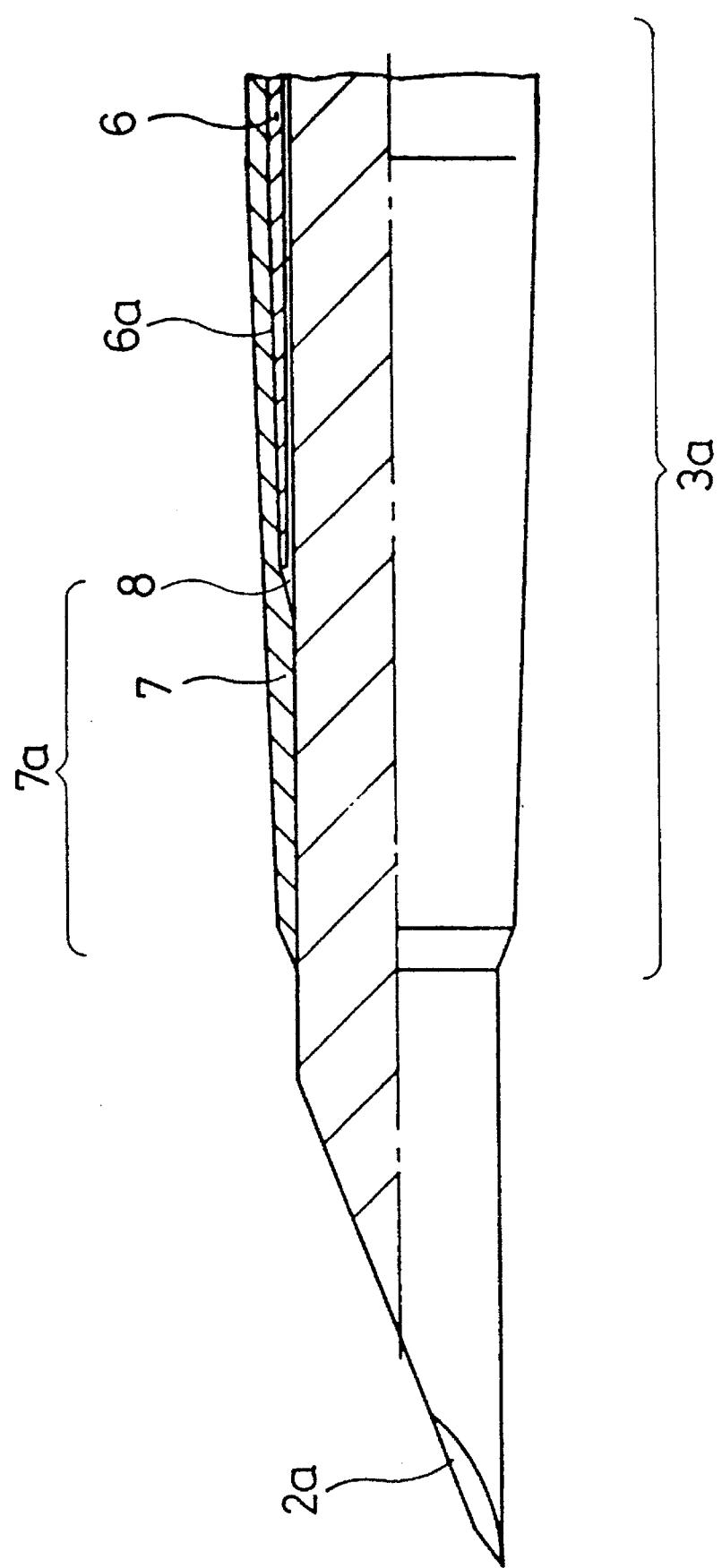
FIG. 3 is a part-sectional enlarged view of the front end portion of the blood vessel piercing instrument of another embodiment of this invention.

Further, the front end portion of the outer tube 3 may also be formed as shown in FIG. 3. In this embodiment, the outside diameter of the front end portion of the metal tubular member 6 becomes smaller toward the front end. By thus forming the front end portion of the metal tubular member 6, the change in bending strength of the outer tube 3 around the front end of the metal tubular member 6 becomes more gradual. This gradual change in the bending strength makes possible smoother bending of the entire front end portion 3a of the outer tube 3 and prevents bending in angles. For this embodiment, it is preferable to form the resin tubular member 7 so that the outside diameter of its front end portion 7a extending beyond the front end of the metal tubular member 6 and the portion around the tapered portion of the metal tubular member 6 (that is, the portion contained in the front end portion 3a of the outer tube 3) becomes gradually smaller toward the front end, as shown in FIG. 3. The blood vessel piercing instrument of this embodiment also preferably has an annular depression 8 between the front end of the metal tubular member 6 and the inside surface of the front end portion 7a of the resin tubular member 7 similar to that of the embodiment in FIG. 2.

In the embodiment of FIG. 3, unlike that of FIG. 2, the inside edge of the front end of the metal tubular member 6 is not cut away, and the entire front end surface of the metal tubular member 6 is a plane perpendicular to the center axis. The inside surface of the resin tubular member 7 opposite the front end of the metal tubular member 6 is so formed that its inside diameter becomes steeply smaller from around the front end of the metal tubular member 6 toward the front end, as in the embodiment of FIG. 2. The annular depression 8 of the embodiment of FIG. 3 thus has a cross section in the shape of a wedge that becomes thinner frontward.

Figure 4:
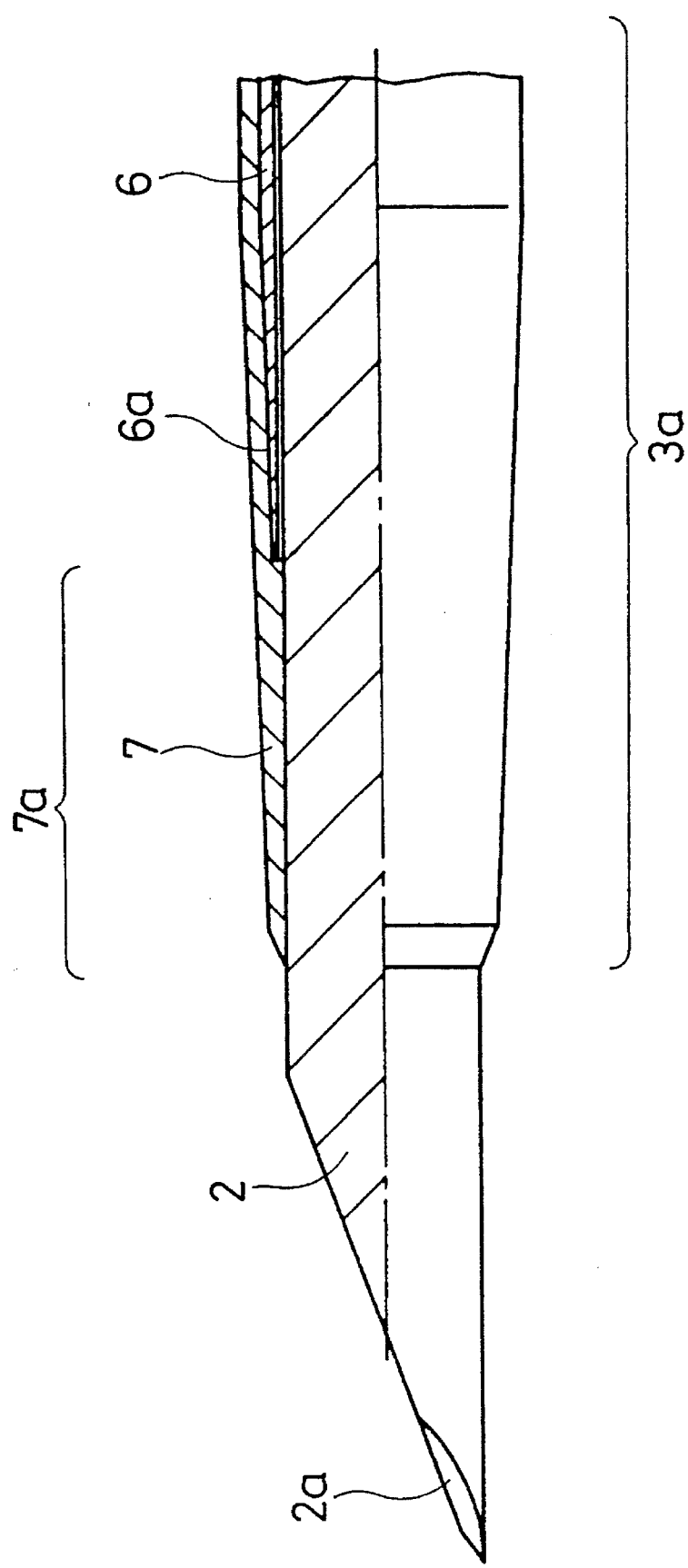
FIG. 4 is a part-sectional enlarged view of the front end portion of the blood vessel piercing instrument of another embodiment of this invention.

The front end portion of the blood vessel piercing instrument of the present invention may also be formed as shown in FIG. 4. The blood vessel piercing instrument of this embodiment does not have an annular depression as described above. The metal tubular member 6 is so formed that the outside diameter of its front end portion becomes gradually smaller toward the front end, and the resin tubular member 7 is so formed that its front end portion 7a extending beyond the front end of the metal tubular member 6 and the portion around the tapered portion of the metal tubular member 6 (that is, the portion contained in the front end portion 3a of the outer tube 3) becomes gradually smaller toward the front end. The outer tube 3 having such an annular depression 8 is made by placing a half-formed resin tubular member over the metal tubular member 6 or inserting a mandrel through the metal tubular member 6 and dipping the metal tubular member 6 and mandrel in a solution of a resin used as the material of the resin tubular member 7 to form a resin tubular member and then hot forming the front end portion of the resin tubular member by means of a metal mold. It can also be made by first forming the resin tubular member 7 with the inside shape as shown in FIG. 4 by means of a metal mold and then inserting the metal tubular member 6 into the resin tubular member 7.

Figure 5:
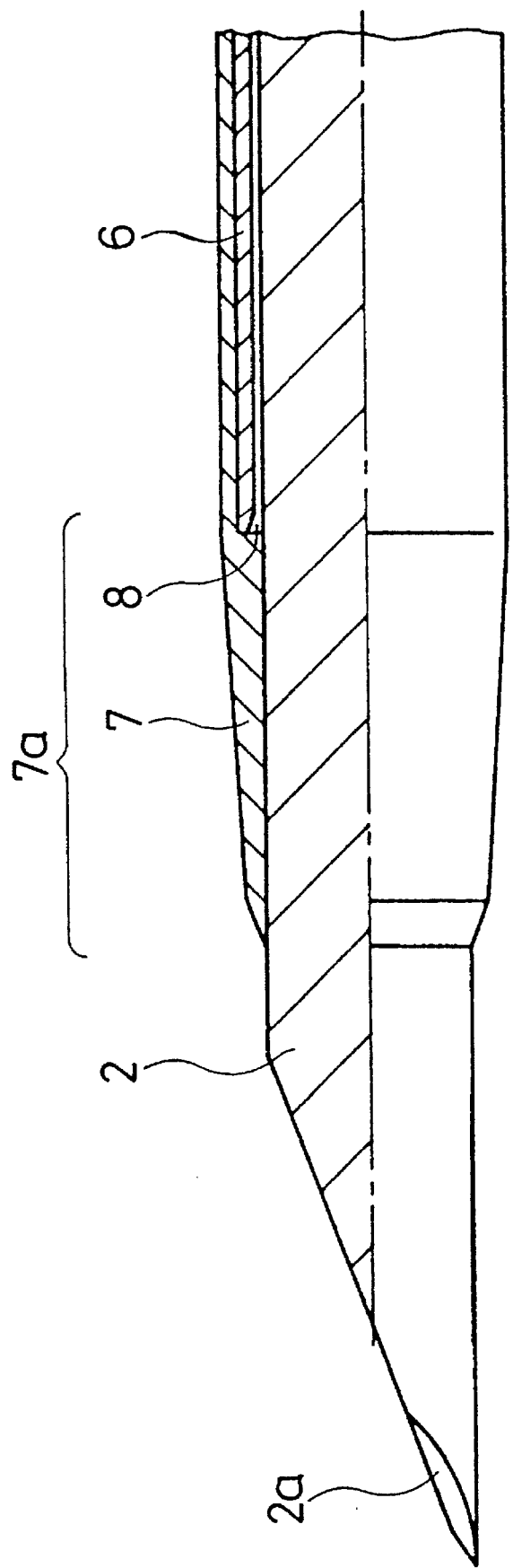
FIG. 5 is a part-sectional enlarged view of the front end portion of the blood vessel piercing instrument of another embodiment of this invention.

The front end portion of the blood vessel piercing instrument of the present invention may also be formed as shown in FIG. 5. In the blood vessel piercing instrument of this embodiment, the metal tubular member 6 is so formed that the inside diameter of its front end becomes larger toward the front end, and an annular depression 8 is formed between the inclined inside surface of the front end of the metal tubular member 6 and the inside surface of the front end portion 7a of the resin tubular member 7.

The metal tubular member 6 in the embodiment of FIG. 5 has the inside surface formed in the shape as described above by cutting away the inside edge of the front end in the same manner as in the embodiment of FIG. 2. The inside surface of the resin tubular member 7 opposite the front end surface of the metal tubular member 6, which may be spaced from or in contact with the front end surface of the metal tubular member 6, is a plane perpendicular to the center axis. The annular depression 8 of the embodiment of FIG. 5 thus has a cross section in the shape of a wedge that becomes thinner rearward.

Figure 10:
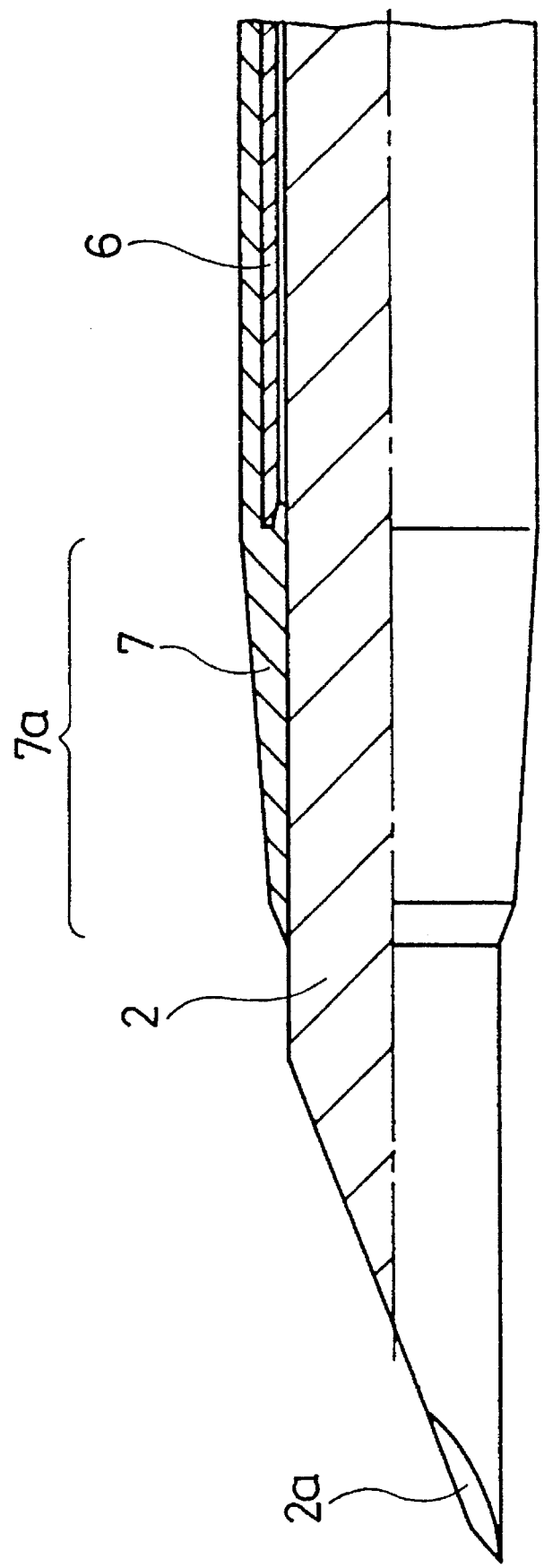
FIG. 10 is a part-sectional enlarged view of the front end portion of the blood vessel piercing instrument of another embodiment of this invention.
Figure 11:
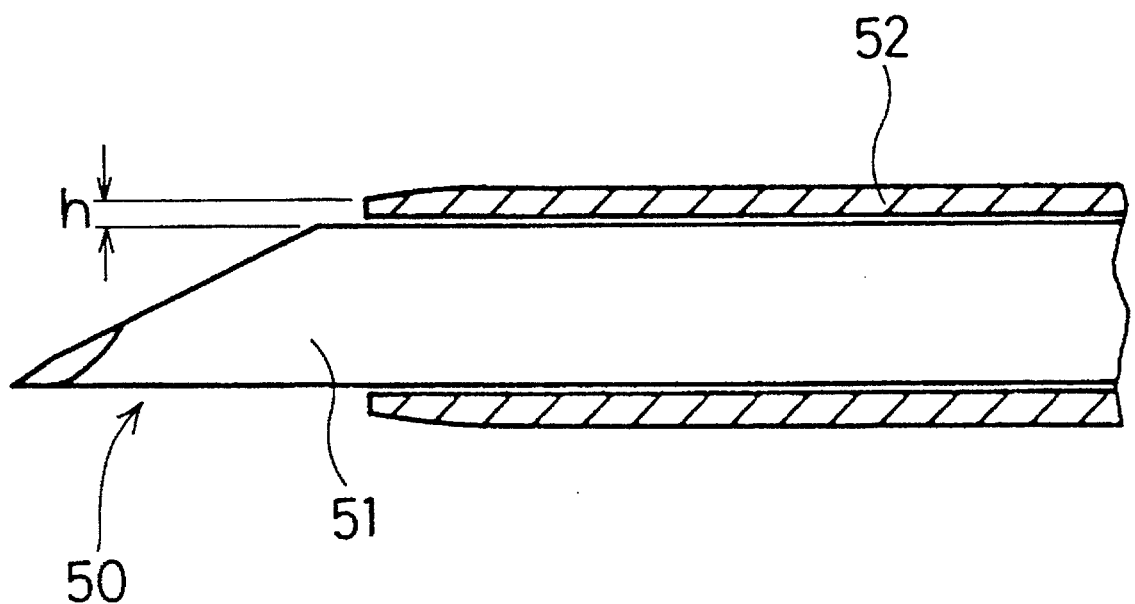
FIG. 11 is a part-sectional enlarged view of the front end portion of a typical conventional blood vessel piercing instrument.

The front end portion of the blood vessel piercing instrument of the present invention may also be formed as shown in FIG. 10. The blood vessel piercing instrument of this embodiment does not have an annular depression as those of the embodiments described above. The resin tubular member 7 is so formed that its front end portion 7a becomes gradually smaller toward the front end.

The metal tubular member 6 of the embodiment of FIG. 10 has the front end formed so that the inside diameter becomes larger frontward by cutting away the inside edge of the front end. The resin tubular member 7 has an annular depression to receive the front end of the metal tubular member 6 in its inside surface opposite the front end of the metal tubular member 6 formed by extending the inner portion of the surface rearward into the space between the inside surface of the metal tubular member 6 and the outside surface of the inner needle 2. By thus forming the resin tubular member 7, the front end of the metal tubular member 6 is dug in the annular depression and not exposed in the inside space of the outer tube 3. Therefore, the guide wire inserted through the outer tube 3 comes into contact with the inside surface of the resin tubular member 7 and does not with the front end of the metal tubular member 6. As the result, the frictional resistance between the guide wire and the outer tube 3 is reduced and the insertion of the guide wire is made easier.

The outer tube 3 of this structure can be made by placing a half-formed resin tubular member over the metal tubular member 6 or inserting a mandrel through the metal tubular member 6 and dipping the metal tubular member 6 and mandrel in a solution of a resin used as the material of the resin tubular member 7 to form a resin tubular member and then hot forming the front end portion of the resin tubular member by means of a metal mold. It can also be made by first forming the resin tubular member 7 with the inside shape as shown in FIG. 10 by means of a metal mold and then inserting the metal tubular member 6 into the resin tubular member 7.

The outer tube 3 of this structure can be made by placing a half-formed resin tubular member over the metal tubular member 6 or inserting a mandrel through the metal tubular member 6 and dipping the metal tubular member 6 and mandrel in a solution of a resin used as the material of the resin tubular member 7 to form a resin tubular member and then hot forming the front end portion of the resin tubular member by means of a metal mold. It can also be made by first forming the resin tubular member 7 with the inside shape as shown in FIG. 10 by means of a metal mold and then inserting the metal tubular member 6 into the resin tubular member 7.

The resin tubular member 7 is preferably made of a fluororesin such as ETFE (ethylene-tetrafluoroethylene), PTFE(polytetrafluoroethylene), FEP(fluoroethylene-propylene) or PFA (polyfluoroacrylate) or an olefinic resin such as polypropylene or polyethylene and has a certain flexibility. The outside diameter of the outer tube 3 is usually within a range of 0.9 to 2.0 mm. The front end portion 7a of the resin tubular member 7 extended beyond the front end of the metal tubular member 6 is preferably within 0.5 to 25.0 mm. The material for the resin tubular member 7 may contain a substance opaque to X rays of 2–30 w % of the resin (barium sulfate or bismuth hypocarbonate, for example). Further, it is preferable to coat the outside surface of the outer tube 3 (the outside surface of the resin tubular member 7) with a lubricating substance (silicone, for example). It is also preferable to coat the outside surface of the inner needle 2 with a lubricating substance (silicone or fluororesin such as ETFE, PTFE, FEP, PFA) in order to reduce the frictional resistance between the outside surface of the inner needle 2 and the inside surface of the outer tube 3, especially the inside surface of the resin tubular member 7.

For the material for forming the metal tubular member 6, superelastic or pseudoelastic alloys are preferable. Superelastic alloys here refer to those alloys generally called shape-memory alloys which show a superelasticity at the body temperature (about 37° C.) at the highest. By the term "superelasticity" it is meant that when an alloy is deformed (bent, stretched or compressed) at service temperature to the extent where conventional metals undergo plastic deformation and the released from deformation, the alloy resumes the original shape without a need for heating.

Preferable superelastic or pseudoelastic alloys include Ti-Ni binary alloys consisting essentially of 49 to 53 atom percents of Ni and the balance of Ti, Cu-Zn binary alloys consisting essentially of 38.5 to 41.5 wt % of Zn and the balance of Cu, Cu-Zn-X ternary alloys consisting essentially of 1 to 10 wt % of X (X=Be, Si, Sn, Aa or Ga) and the balance of Cu, and Ni-Al binary alloys consisting essentially of 36 to 38 atom % of Al and the balance of Ni. The Ti-Ni alloy is especially preferable.

Mechanical properties may be properly controlled by replacing part of Ti-Ni alloy by 0.01 to 10.0 atom % of X to form Ti-Ni-X alloys wherein X is Co, Fe, Mn, Cr, V, Al, Nb, W or B or replacing part of Ti-Ni alloy by 0.01 to 30.0 atom % of X to form Ti-Ni-X alloys wherein X is Cu, Pd or Zr and/or selecting the conditions of cold working and/or final heat treatment.

When the metal tubular member 6 is made of such a superelastic metal, the metal tubular member 6 has an appropriate rigidity at its basal (rear end) portion and becomes more flexible toward the front end. By thus forming the metal tubular member 6, the function of the blood vessel piercing instrument of this invention is improved. The wall thickness of the metal tubular member 6 is preferably within a range of 20 to 150 µm, taking account of the required rigidity and flexibility.

Next the outer tube hub 5 is described.

The outer tube hub 5, as shown in FIG. 6, has a bore which allows the inner needle 2 to be passed through into the outer tube 3 and the rear end formed so that it can engage with the inner needle hub 4 described above. The outer tube hub 5 has a flange-like grasp 5a formed at the middle part of its length for holding the blood vessel piercing instrument 1 when the instrument 1 is thrust into the blood vessel. The bore is formed in a larger diameter in the front end portion of the outer tube hub 5 and the front end portion of the bore is formed in the shape of a funnel to receive and hold the rear end of the outer tube 3. The resin tubular member 7 of the outer tube 3 has a flange 7b formed at the rear end, and the rear end of the metal tubular member 6 protrudes beyond the rear end of the resin tubular member 7, as shown in FIG. 6. The rear ends of the metal tubular member 6 and resin tubular member. 7 are inserted in the bore and bonded to the outer tube hub 5 by means of an adhesive 11 filled in the gap between the tubes 6 and 7 and the outer tube hub 5. The outer tube 3 may also be attached to the outer tube hub 5 by stacking using a short metal tubular member inserted into the outer tube 3 from the rear end.

Figure 7:
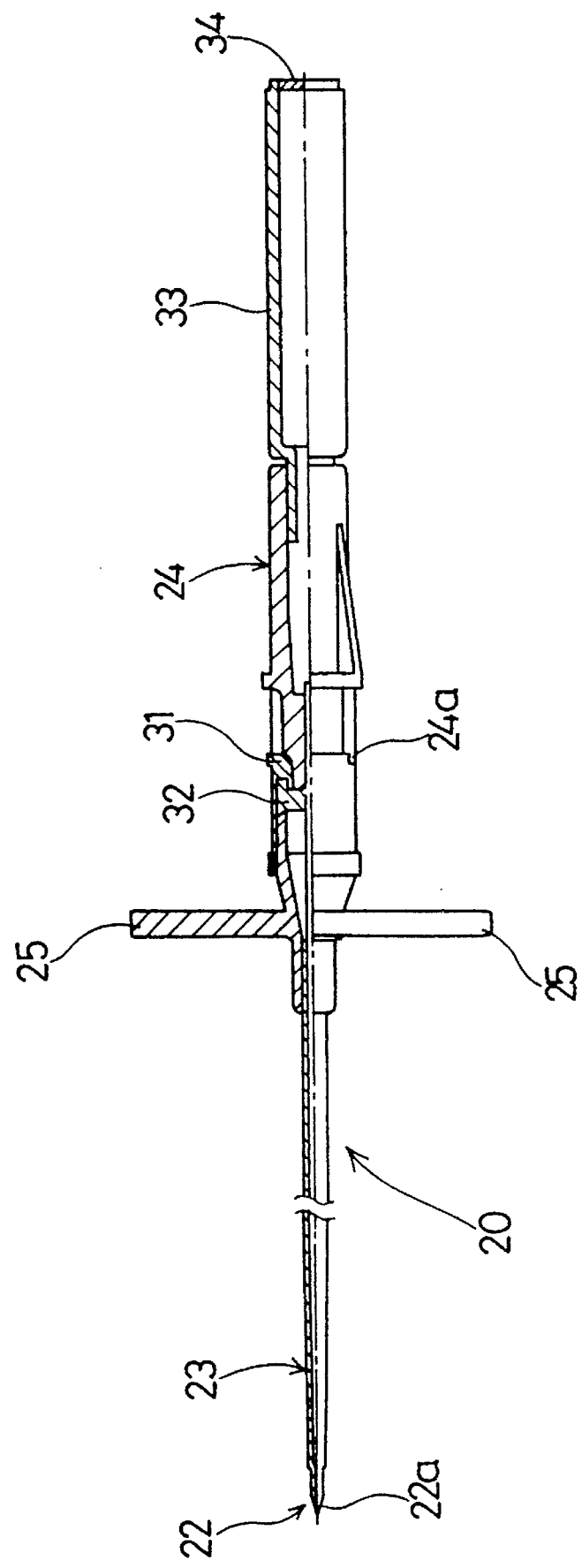
FIG. 7 is a part-sectional view of the middle to rear end portion of the blood vessel piercing instrument of another embodiment of this invention.

Next the embodiment of the blood vessel piercing instrument of the present invention shown in FIG. 7 is described.

The blood vessel piercing instrument 20 of this invention is different from the blood vessel piercing instrument 1 of the above embodiment in that the inner needle of this embodiment is made of a hollow member.

The blood vessel piercing instrument 20 comprises an outer tube assembly consisting of an outer tube 23 and an outer tube hub 25 attached to the rear end portion of the outer tube 23 and an inner needle assembly consisting of a hollow inner needle 22 which is extractably inserted in the outer tube assembly and has a piercing edged surface 22a formed at the front end protruding from the outer tube 23 and an inner needle hub 24 which is attached to the rear end portion of the inner needle 22 and engages with the rear end of the outer tube hub 25.

The outer tube hub 25 has a tubular member 31 attached to the rear end portion. An elastic valve member 32 is provided between the bore of the outer tube hub 25 and the tubular member 31 to allow a guide wire and catheter to be inserted through it in the liquid tight fashion and close the bore of the outer tube hub 25 when neither a guide wire nor a catheter is inserted.

Figure 8:
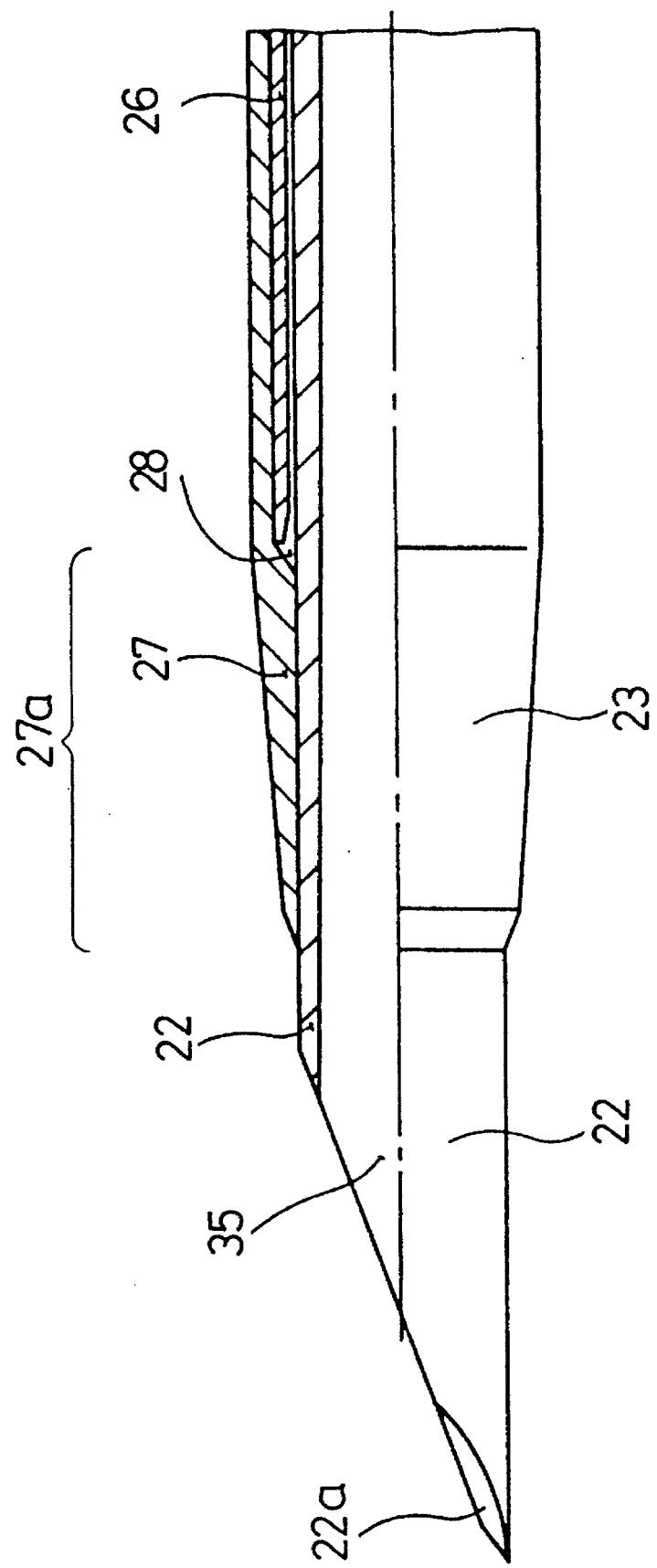
FIG. 8 is a part-sectional enlarged view of the front end portion of the blood vessel piercing instrument of another embodiment of this invention.

The outer tube 23, as shown in FIG. 8, consists of a metal tubular member 26 made of a superelastic metal and a resin tubular member 27 which covers the outside surface of the metal tubular member 26 and has the front end portion extending beyond the front end of the metal tubular member 26. The inside diameter of the front end portion of the resin tubular member 27 is smaller than the inside diameter of the metal tubular member 26 and approximately equal to the outside diameter of the inner needle 22.

The inner needle assembly comprises an inner needle 22, an inner needle hub 24 attached to the rear end of the inner needle 22, and a cap 33 detachably attached to the rear end of the inner needle hub 24 as shown in FIG. 7.

The inner needle 22 has a piercing edged surface 22a formed at the front and has such a length that it extends through the outer tube 23 and the edged surface 22a protrudes from the front end of the outer tube 23. In this embodiment, a hollow needle is used for the inner needle 22. A basic difference between the blood vessel piercing instrument 20 of this embodiment and that of FIG. 1 is in that a hollow inner needle is used in this embodiment. The front end portion of the inner needle hub 24 is formed in a shape which fits to the rear end portion of a tubular member 31 attached to the rear end portion of the outer tube hub 25. The cap 33 has a filter 34 which allows air to pass but does not pass blood provided at the rear end. By using such a filter, the blood entering the inner needle 22 can be prevented from flowing out. A projection 24a, which serves as a securing mechanism for stopping the turning movement of the inner assembly and fixing the position of the tip of the piercing edged surface 22a, is provided on the front end of the inner needle hub 24.

The inner needle hub 24 and the cap 33 have preferably such a degree of transparency that the flashback of blood (inflow of blood into the inner needle hub) can be viewed through them.

For the material of the inner needle hub 24, thermoplastic resins such as polypropylene, polyethylene, polycarbonate, and polystyrene can be used. Among these resins, those having a certain degree of transparency are preferable. The inner needle 22 and the inner needle hub 24 may be attached by means of an adhesive or a solvent, or by heating the inner needle 22 by electromagnetic induction and fusing the inner needle hub 24 made of a thermoplastic resin.

The outer tube assembly comprises an outer tube 23 inserted into the blood vessel and an outer tube hub 25 attached to the rear end portion of the outer tube 23. The outer tube 23 is open at the front end with a diameter which allows the front end (piercing head) of the inner needle 22 to protrude, as shown in FIGS. 7 and 8. The outer tube 23 consists of a metal tubular member 26 made of a superelastic metal and a resin tubular member 27 covering the outside surface of the metal tube 26, as shown in FIG. 8. The front end portion of the resin tubular member 27 extends beyond the front end of the metal tubular member 26. The outside diameter of the front end portion 27a of the resin tubular member 27 (more specifically the portion extending beyond the front end of the metal tubular member 26) becomes gradually smaller toward the front end and that of the short front end portion becomes steeply smaller to the front end. The inside diameter of the front end portion 27a is equal to or a little larger or smaller than the outside diameter of the inner needle 22 so that a step or gap is not formed between the outside surface of the inner needle 22 and the front end of the resin tubular member 27.

Since a step or gap is thus practically not formed between the outside surface of the inner needle 22 and the front end of the outer tube 23, this blood vessel piercing instrument 20 causes less pain to the patient when it is thrust into the blood vessel. Further, since the front end portion of the outer tube 23 is formed of a soft resin, the possibility that the front end of the outer tube 23 may hurt the wall of the blood vessel when the inner needle 22 is pulled off and a guide wire is inserted significantly diminishes. Furthermore, since the front end portion made of a soft resin elastically deforms to accommodate its shape to the wire inserted, insertion of a guide wire is made easier than when the front end portion of the outer tube 23 is made of a metal.

It is preferable to form an annular depression 28 between the front end of the metal tubular member 26 and the inside surface of the front end portion 27a of the resin tubular member 27. By forming such an annular depression 28, the elastic bending of the resin tubular member 27 is made easier. The outer tube 23 having such an annular depression 28 can be made by the method described above.

Although, in the blood vessel piercing instrument of this embodiment, the entire inside surface of the front end portion 27a of the resin tubular member 27 has a substantially uniform diameter and is in contact with the outside surface of the inner needle 22, the front end portion 27a may also be in such a form that only the inside surface of its short front end portion is in contact with the outside surface of the inner needle 22.

Figure 9:
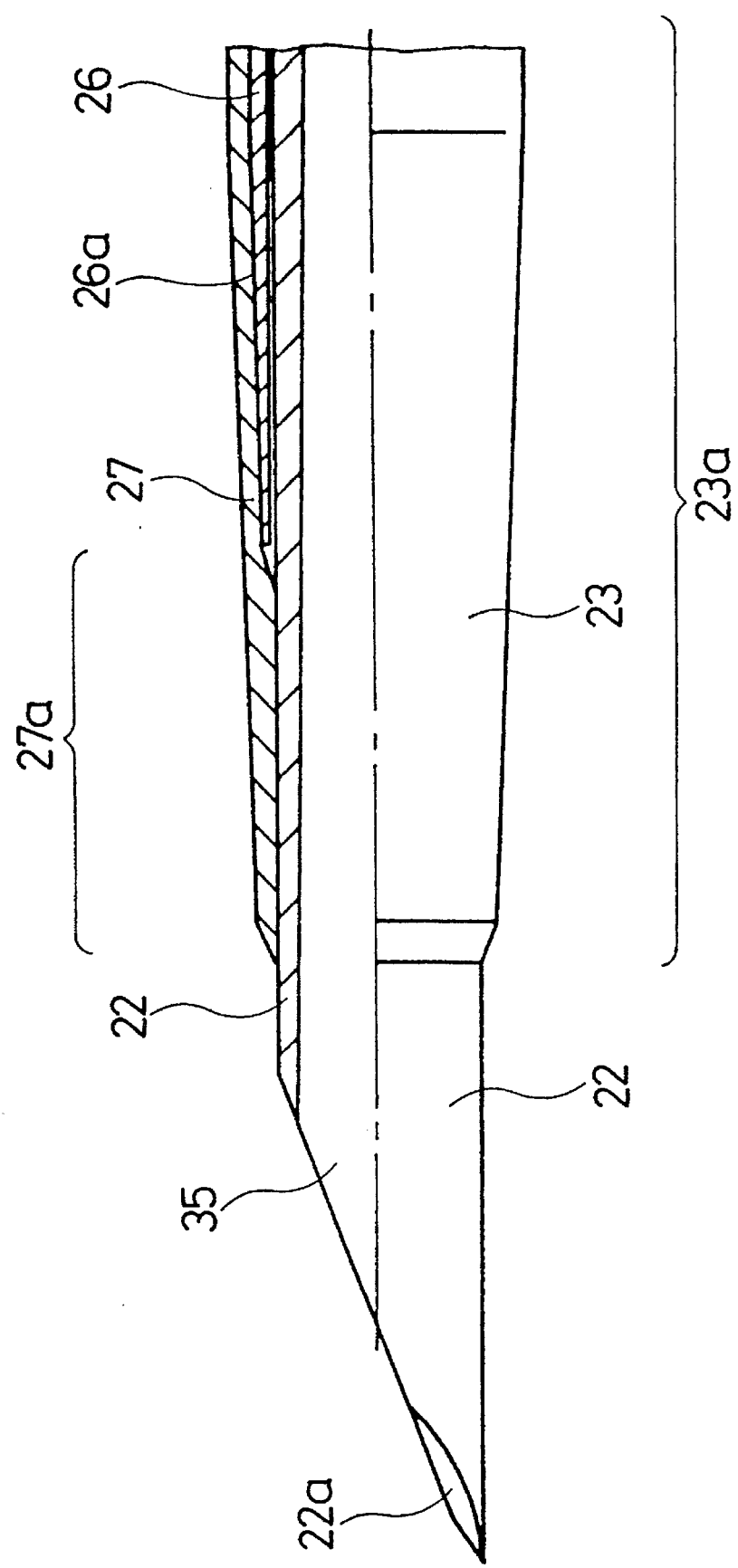
FIG. 9 is a part-sectional enlarged view of the front end portion of the blood vessel piercing instrument of another embodiment of this invention.

Further, the front end portion of the outer tube 23 may also be formed as shown in FIG. 9. In this embodiment, the outside diameter of the front end portion of the metal tubular member 26 becomes smaller toward the front end. By thus forming the front end portion of the metal tubular member 26, the change in bending strength of the outer tube 23 around the front end of the metal tubular member 26 becomes more gradual. This gradual change in the bending strength makes possible smoother bending of the entire front end portion 23a of the outer tube 23 and prevents bending in angles. For this embodiment, it is preferable to form the resin tubular member 27 so that the outside diameter of its front end portion 27a extending beyond the front end of the metal tubular member 26 and the portion around the tapered portion of the metal tubular member 26 (that is, the portion contained in the front end portion 23a of the outer tube 23) becomes gradually smaller toward the front end, as shown in FIG. 9.

The blood vessel piercing instrument 20 of this embodiment also has an annular depression 28 between the front end of the metal tubular member 26 and the inside surface of the front end portion 27a of the resin tubular member 27 similar to that of the embodiment in FIG. 8.

The blood vessel piercing instrument 20 of this embodiment may also has the structures of the front end portion as shown in FIGS. 4, 5 and 10.

The resin tubular member 27 is preferably made of a fluororesin such as ETFE, PTFEP, FEP or PFA or an olefinic resin such as polypropylene or polyethylene and has a certain flexibility. The outside diameter of the outer tube 23 is usually within a range of 0.9 to 2.0 mm. The front end portion of the resin tubular member 27 extended beyond the front end of the metal tubular member 26 is preferably 0.5 to 25.0 mm. The material for the resin tubular member 27 may contain a substance opaque to X rays of 2~30 w % of the resin (barium sulfate or bismuth hypocarbonate, for example). Further, it is preferable to coat the outside surface of the outer tube 23 (the outside surface of the resin tubular member 27) with a lubricating substance (silicone, for example). It is also preferable to coat the outside surface of the inner needle 22 with a lubricating substance (silicone or fluororesin such as ETFE, PTFE, FEP, PFA) in order to reduce the frictional resistance between the outside surface of the inner needle 22 and the inside surface of the outer tube 23, especially the inside surface of the resin tubular member 27.

For the material for forming the metal tubular member 26, superelastic or pseudoelastic alloys are preferable.

Preferable superelastic or pseudoelastic alloys include Ti-Ni binary alloys consisting essentially of 49 to 53 atom percents of Ni and the balance of Ti, Cu-Zn binary alloys consisting essentially of 38.5 to 41.5 wt % of Zn and the balance of Cu, Cu-Zn-X ternary alloys consisting essentially of 1 to 10 wt % of X (X=Be, Si, Sn, Al or Ga) and the balance of Cu, and Ni-Al binary alloys consisting essentially of 36 to 38 atom % of Al and the balance of Ni. The Ti-Ni alloy is especially preferable.

Mechanical properties may be properly controlled by replacing part of Ti-Ni alloy by 0.01 to 10.0 atom % of X to form Ti-Ni-X alloys wherein X is Co, Fe, Mn, Cr, V, Al, Nb, W or B or replacing part of Ti-Ni alloy by 0.01 to 30.0 atom % of X to form Ti-Ni-X alloys wherein X is Cu, Pd or Zr and/or selecting the conditions of cold working and/or final heat treatment. When the metal tubular member 26 is made of such a superelastic or pseudoelastic metal, it preferably has an appropriate rigidity at its basal (rear end) portion and becomes more flexible toward the front end. By thus forming the metal tubular member 26, the function of the blood vessel piercing instrument is improved.

The outer tube hub 25, as shown in FIG. 7, has a tubular member 31 attached to its rear end portion. The tubular member 31 is provided inside it with an elastic valve member 32 which openably closes part of the cross section of the bore of the outer tube hub 25. The valve member 32 has a disk-like shape and an openable part for allowing the inner needle 22 and a guide wire to be inserted through in a liquid-tight fashion. This openable part closes when neither the inner needle 22 nor a guide wire is inserted, preventing the blood from flowing out.

For the valve member 32 which performs such a function, a disk-shaped member made of a soft material such as silicone rubber, butadiene rubber, or styrene-elastomer (SBS elastomer, SEBS elastomer, for example) is preferable. The openable part of the valve member 32 can be formed by making incisions such as so called Y cut or crucial (+) cut in the valve member. An openable part formed by first and second incisions on each side of the valve member which do not reach the other side and intercross at the center of the valve member is preferable.

For the material of the outer tube hub 25, thermoplastic resins such as polypropylene, polyethylene, polycarbonate, and polystyrene can be used. Especially those of them having a certain degree of transparency are preferable. The inner needle 22 and the inner needle hub 25 can be attached by the same methods as described above.

Next how to use this blood vessel piercing instrument 1 of this invention is described.

The inner needle 2 is inserted in the outer tube 3 from the rear end of the outer tube hub 5 before use, as shown in FIG.

1. When the inner needle hub 4 is engaged with the rear end of the outer hub 5, the piercing edged surface 2a of the inner needle 2 protrudes from the front end of the outer tube 3 and the blood vessel piercing instrument 1 is ready to be thrust into blood vessel. The blood vessel piercing instrument 1 in this state is grasped at the outer tube hub 5 and thrust into the blood vessel. The inner needle assembly is then pulled off from the outer tube assembly. This makes it possible for the blood to flow out through the inside of the outer tube 3, and it is ascertained by the blood flowing out that the front end of the outer tube 3 is in the blood vessel. Next a guide wire is inserted into the blood vessel through the outer tube 3. After a certain length of the guide wire is inserted into the blood vessel, the outer tube 3 is removed and then a catheter such as blood vessel dilatation catheter or catheter for the roentogenographic visualization of the blood vessels is slid on the guide wire and inserted into the blood vessel.

In the blood vessel piercing instrument of this invention, as described above, neither a step nor gap is formed between the outside surface of the inner needle and the tip of the outer tube (the resin tubular member). Because of this structure, the blood vessel piercing instrument of this invention causes less pain to the patient when it is thrust into the blood vessel.

Further, the front end portion of the outer tube is formed of a soft resin. This significantly reduces the possibility that the front end of the outer tube may hurt the wall of the blood vessel after the inner needle is removed and when a guide wire is inserted significantly diminishes.

Furthermore, the front end portion of the outer tube is made of a soft resin and elastically deforms to accommodate its shape to a guide wire inserted. Also, the metal tubular member of the outer tube made of a superelastic metal has a high strength and elasticity and therefore the entire outer tube can bend smoothly. These makes easier the insertion of a guide wire and prevents the outer tube from bending in angles after the inner needle is removed or when a guide wire is inserted.

We claim:

1. A blood vessel piercing instrument comprising an outer tube assembly and an inner needle assembly, said outer tube assembly comprising an outer tube and an outer tube hub attached to a rear end portion of said outer tube, and said outer tube comprising a metal tubular member made of a superelastic or pseudoelastic metal and a resin tubular member which covers an outside surface of the metal tubular member and has a front end portion extending beyond a front end of the metal tubular member, said inner needle assembly comprising an inner needle which is extractably inserted in said outer tube assembly and has a piercing edged surface formed at a front end protruding from said outer tube and an inner needle hub which is attached to a rear end portion of said inner needle assembly and engages with a rear end of said outer tube hub, an inside diameter of said front end portion of said resin tubular member is smaller than an inside diameter of said metal tubular member and substantially equal to an outside diameter of said inner needle.

2. The blood vessel piercing instrument of claim 1, wherein the outside diameter of said resin tubular member becomes gradually smaller toward the front end portion of said resin tubular member.

3. The blood vessel piercing instrument of claim 1, wherein an outside diameter of said metal tubular member becomes gradually smaller toward the front end of said metal tubular member.

4. The blood vessel piercing instrument of claim 1, wherein an annular depression is formed between the front end of said metal tubular member and an inside surface of said resin tubular member.

5. The blood vessel piercing instrument of claim 1, wherein an inside surface of the front end of said resin tubular member is in close contact with an outside surface of said inner needle.

6. The blood vessel piercing instrument of claim 1, wherein an inside surface of said resin tubular member is in close contact with an outside surface of said metal tubular member.

* * * * *

UNITED STATES PATENT AND TRADEMARK OFFICE
CERTIFICATE OF CORRECTION

PATENT NO. : 5,522,832
DATED : June 4, 1996
INVENTOR(S) : Takahiro KUGO et al

It is certified that error appears in the above-indentified patent and that said Letters Patent is hereby corrected as shown below:

In Column 7, line 9, delete "Aa" and insert -- Al --.

Signed and Sealed this

Twenty-ninth Day of October 1996

Attest:

BRUCE LEHMAN

Attesting Officer    Commissioner of Patents and Trademarks